United States Patent [19]

Antonelli et al.

[11] 3,943,069
[45] Mar. 9, 1976

[54] PROCESS FOR THE PRODUCTION OF SILVER-BASED CATALYSTS SUITABLE FOR THE PRODUCTION OF ETHYLENE OXIDE

[75] Inventors: Giambattista Antonelli, Brugherio (Milan); Natale Ferlazzo; Giancarlo Aglietti, both of Milan, all of Italy

[73] Assignee: Societa' Italiana Resine S.I.R. S.p.A., Milan, Italy

[22] Filed: Nov. 28, 1973

[21] Appl. No.: 419,834

[30] Foreign Application Priority Data
Nov. 30, 1972 Italy .................................. 32272/72

[52] U.S. Cl............ 252/443; 252/463; 252/466 PT; 252/476; 260/348 R
[51] Int. Cl.² .......................................... B01J 27/20
[58] Field of Search....... 252/476, 443, 463, 466 PT

[56] References Cited
UNITED STATES PATENTS

| | | | |
|---|---|---|---|
| 2,446,132 | 7/1948 | Evans | 252/476 X |
| 2,477,435 | 7/1949 | Aries | 252/476 X |
| 2,709,173 | 5/1955 | Brengle et al. | 252/476 X |
| 2,773,844 | 12/1956 | Carlson et al. | 252/476 X |
| 3,501,417 | 3/1970 | De Maio | 252/443 |
| 3,563,913 | 2/1971 | Krijger et al. | 252/463 |
| 3,563,914 | 2/1971 | Wattimena | 252/463 |
| 3,575,888 | 4/1971 | Long | 252/443 X |
| 3,664,970 | 5/1972 | De Maio | 252/476 X |
| 3,725,307 | 4/1973 | Brown et al. | 252/476 X |
| 3,773,693 | 11/1973 | Calcayno et al. | 252/463 X |

*Primary Examiner*—Helen M. S. Sneed
*Attorney, Agent, or Firm*—Sughrue, Rothwell, Mion, Zinn & Macpeak

[57] ABSTRACT

Silver-based catalysts suitable for the production of ethylene oxide are prepared by impregnating a granular support with a decomposable silver salt, drying the impregnated products, and finally heat-treating the dried product at a high temperature, in a gaseous atmosphere containing at least 1 % by volume of carbon dioxide.

19 Claims, 1 Drawing Figure

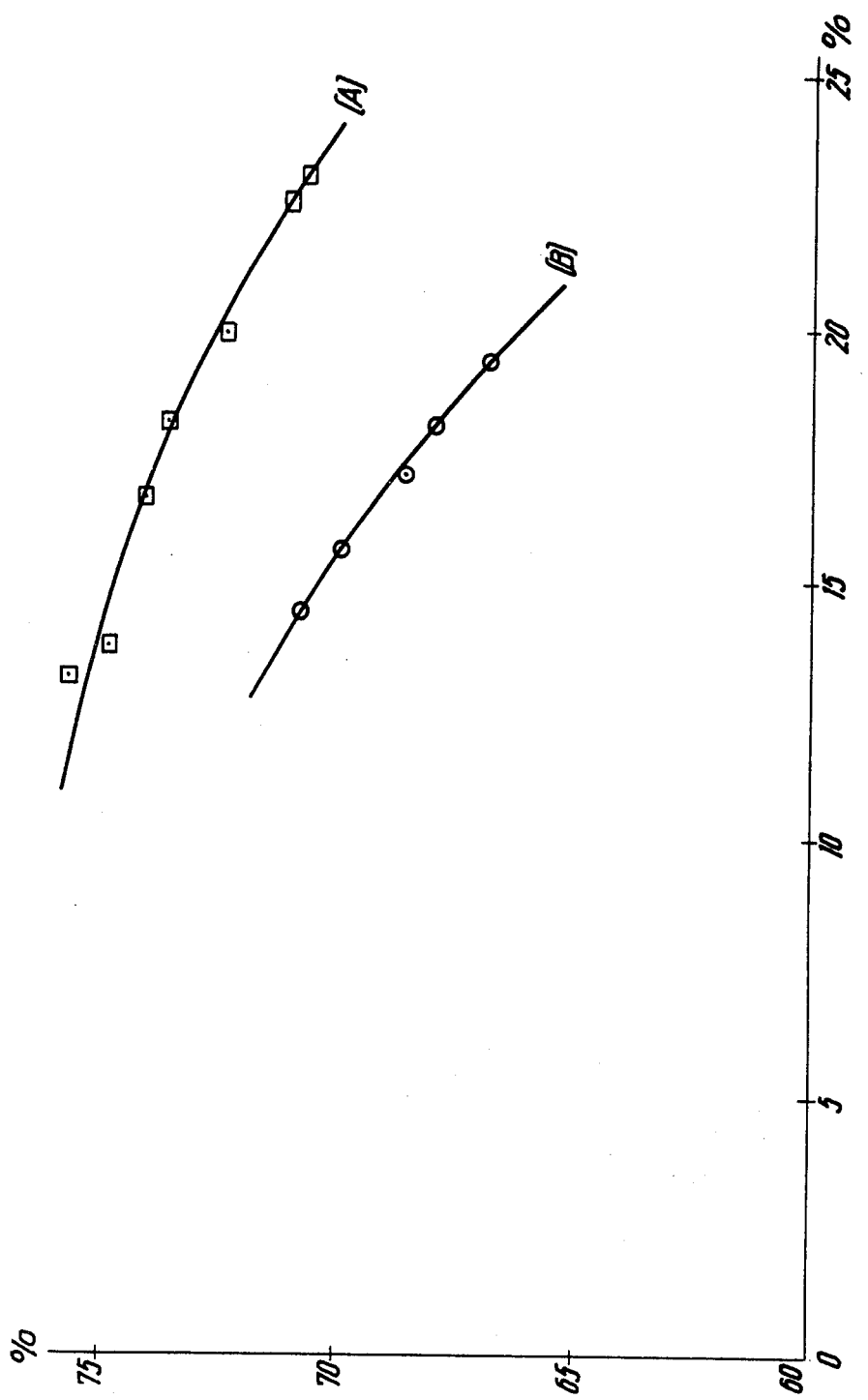

PROCESS FOR THE PRODUCTION OF SILVER-BASED CATALYSTS SUITABLE FOR THE PRODUCTION OF ETHYLENE OXIDE

The present invention relates to an improvement in the process for the production of ethylene oxide, which comprises the oxidation of ethylene with oxygen in the presence of an active silver-based catalyst.

The invention also relates to the active silver-based catalyst for use in the oxidation of ethylene to to ethylene oxide, which is obtained by impregnation of an inert granular support with a decomposable silver salt followed by a specific decomposition of the said salt on the support.

DESCRIPTION OF THE PRIOR ART

In a process that is widely used in the art, ethylene oxide is obtained by contact of ethylene with oxygen on silver-based catalysts at high temperatures. Such catalysts normally consist of an inert granular support on which silver has been deposited, and smaller quantities of other metals such as platinum, gold, palladium, barium, and calcium may also be present.

These latter are described as activators of the oxidation of ethylene.

In a process known in the art, the silver-based catalysts are prepared by impregnation of an inert particulate support with a decomposable silver salt.

A particularly suitable salt for this purpose is silver lactate, which is used either in the molten state or in solution.

The impregnated support is then dried and finally treated at a high temperature, with consequent thermal decomposition of the silver salt and deposition of metallic silver on the support. The thermal decomposition is normally carried out at temperatures of from 250° to 400°C in the presence of air.

According to the description in Italian Pat. No. 912,750, improved catalysts are obtained when the heat treatment described is carried out initially in an atmosphere of nitrogen and then in an atmosphere of nitrogen and oxygen, with a gradual increase in the content of oxygen up to about 20% by volume in the gaseous mixture.

A further improvement in the preparation of the silver catalyst is described in German Offenlegungsschrift No. 2,253,719. According to the application, the thermal decomposition of the silver salt is again carried out in a nitrogen-oxygen gas atmosphere with progressively increasing quantities of oxygen, the essential characteristic of the process of the above reference consisting in that the gases evolved as a result of the thermal decomposition of the silver salt are allowed to flow continuously through the particles of the catalyst being formed.

According to the processes of the Italian patent and the German Offenlegungasschrift silver-based catalysts are obtained having improved mechanical properties, better activity and selectivity in the oxidation of ethylene to ethylene oxide.

SUMMARY

It has now been found that the characteristics of the supported silver-based catalysts can be further substantially improved by the use of special measures in the phase of the catalyst preparation in which the decomposable silver salts are treated at high temperatures to deposit metallic silver on the support.

One object of the present invention is thus supported silver-based catalysts having good mechanical properties and high values of activity and selectivity in the production of ethylene oxide..

Another object of the present invention is a process for the preparation of ethylene oxide that involves bringing ethylene and oxygen into contact with the said catalysts.

Other objects of the present invention will appear from the following description.

The present invention is based essentially on the discovery that the nature of the silver deposited as a result of the thermal decomposition of the decomposable silver salts is strongly influenced by the composition of the gaseous environment with which the catalyst being formed is in contact.

More particulary, it has been found that particularly favourable results are obtained when a gaseous atmosphere containing substantial quantities of carbon dioxide is maintained at all times during the thermal decomposition of the decomposable silver salt.

The process for the preparation of the catalyst of the present invention therefore comprises the impregnation of an inert particulate support with a decomposable silver salt and the subsequent decomposition of the said salt in a gaseous atmosphere containing substantial quantities of carbon dioxide.

By substantial quantities of carbon dioxide it is meant that the quantity of carbon dioxide in the gas in contact with the catalyst should never be less than about 1% by volume and preferably not less than about 50% by volume.

It has been found that when the decomposition is carried out in the presence of carbon dioxide and in the range of the other conditions that will be described later, one obtains a silver deposit in the form of crystals of unusually uniform size in the range from about 0.1 to 0.3 micron.

Besides having good mechanical properties, particularly toughness, the catalysts prepared in this way exhibit high activity and selectivity in the oxidation of ethylene to ethylene oxide.

It should also be pointed out that the effect exerted by carbon dioxide during the preparation of the catalyst cannot be observed with the use of other gases.

On the other hand, it is known that carbon dioxide exerts a moderating effect during the reaction for the preparation of ethylene oxide when the carbon dioxide is fed to the catalyst together with the ethylene and the oxygen.

However, the catalysts prepared in accordance with prior art do not attain the results obtainable with those of the application even when carbon dioxide is used in the gaseous feed.

The decomposable silver salts that can be used for the purposes of the present invention are those that decompose at high temperatures, such as the salts of lactic, citric, matlic, and isomalic acids, and among these, silver lactate is preferred.

The support materials are those normally used in the art, such as alumina, silicon carbide, magnesium oxide, or combinations of these materials.

A particularly useful support for this purpose is α-alumina that has undergone an activation process by treatment at temperatures above about 1000°C and that has a surface area of about 0.01 to 1.0 m²/gram, a porosity of about 10 to 50 percent, and an average pore diameter of about 20 to 180 microns.

The support is normally used in the form of spherules having a diameter in the range from about 4 to 9 mm.

In the process of the present invention, the support is first impregnated with a decomposable silver salt.

The impregnation procedures are known in the art and do not form part of the process of the present invention.

For example, the silver lactate may be used molten or in the form of a solution in lactic acid or in aqueous lactic acid.

In this last case, the lactic acid is usually present in a molar excess of about 20 to 200 percent with respect to the number of moles necessary for complete conversion of the silver present into the salt.

The impregnation is normally carried out at temperatures of from about 60° to 115°C, and the salt is used in a quantity such as to ensure a quantity of silver of from about 7 to 30% by weight with respect to the support in the finished catalyst.

Also in the impregnation phase, the promotors of the oxidation of ethylene, such as palladium, gold, or platinum, may be added, normally in quantities of from about 0.01 to 1.0% by weight with respect to the metallic silver.

Such promotors may be added in the form of metals themselves; alternatively, the products known commercially as palladium/carbon, platinum/carbon, or carbon impregnated with colloidal platinum may be used.

It is preferable in every case to use such materials in the form of granules having a size of from about 0.1 to 100 microns.

The activator metals or the palladized carbon, platinized carbon, or carbon impregnated with colloidal platinum are normally suspended in the solution of the decomposable silver salts, and the support is impregnated with the suspension obtained in this way.

Other promotors such as barium and calcium may be added to the solution of the silver salt, for example in the form of salts of lactic acid and in quantities of from about 0.1 to 5 moles per 100 gram atoms of silver.

Finally, the impregnation of the support particles may be conveniently carried out in an apparatus of the rotary evaporator type, the temperature being maintained within the limits specified above.

The impregnated particles are then dried.

For this purpose, it is convenient to cause the particles to roll in a stream of air, the temperature being gradually raised to a maximum value not exceeding 160°C and in times of from about 1 to 10 hours.

In the process of the present invention, the product from the drying is heat-treated at a temperature of from about 270° to 350°C in a gaseous environment containing, at all times during the treatment, a quantity of carbon dioxide not less than about 1% by volume and preferably not less than about 50% by volume.

Particularly favourable results are obtained by the use of a quantity of carbon dioxide greater than about 70% by volume and temperatures of from about 290° to 310°C.

More particularly, according to the process of the present invention, the support particles impregnated with the decomposable silver salt and then dried are placed in an atmosphere of carbon dioxide, and the temperature is then raised to values in the range from about 270° to 350°C and preferably from about 290° to 310°C.

Oxygen is then added to the gaseous mixture in steadily increasing quantities up to an oxygen content of not less than about 0.01% by volume and preferably in the range of values from about 1 to 20% by volume in the gas.

The oxygen introduction time will be conveniently maintained at values greater than about 5 hours and preferably at values in the range from about 7 to 10 hours.

During the heat treatment, the temperature is kept at values in the ranges indicated above, and it is also convenient to cause the gas to flow continuously through the particles of the catalyst being formed by recycling of the gas.

For this purpose, the gas is recycled through the bed of particles at a rate of about 10 to 10,000 liters per hour per kg of catalyst being formed.

The fraction of the gaseous mixture corresponding to the quantity of oxygen gradually introduced is preferably continuously bled off in this phase.

Moreover, it is possible to use pure oxygen (purity 99 percent or more) or commercial oxygen having a purity of about 95 percent.

It is also possible, though not preferred, to use gases containing oxygen such as air.

Instead of recycling the gas, it is also possible to feed in continuously a gas stream consisting initially of carbon dioxide and then of carbon dioxide-oxygen mixtures with progressively increasing quantities of oxygen up to the values indicated and to bleed the gas off continuously after contact with the bed of particles of the catalyst being formed. However, this procedure is not favored for economic reasons.

The heat treatment of the catalyst may be carried out at atmospheric pressure, but it is also possible to use higher pressures, e.g., up to 20 kg/cm$^2$.

After cooling, the catalyst is ready for use.

The catalyst obtained in this way possesses good mechanical properties, which make it particularly suitable for use for long periods in the industrial production of ethylene oxide.

Moreover, as can be seen in the electron microscope, the catalysts of the present invention contain metallic silver in the form of crystals of unusually uniform size in the range of values from 0.1 to 0.3 micron.

Such catalysts are highly active and selective in the processes for the preparation of ethylene oxide by oxidation of ethylene with oxygen.

Such processes are normally carried out at temperatures of from about 200° to 330°C, at pressures of from about 1 to 30 atm, and with contact times of from about 1 to 10 seconds.

Moreover, the process for the preparation of the catalyst in accordance with the present invention is advantageous in that the operations for the decomposition of the decomposable silver salts can be easily automated and can be carried out in the actual reactor for the production of ethylene oxide.

The following experimental examples illustrate the invention further without limiting it in any way.

EXAMPLE 1

17.0 grams of silver oxide, 1.6 grams of hydrogen peroxide, and 0.463 grams of barium hydroxide having 8 molecules of water of crystallization are added to 25 grams of lactic acid.

The solution obtained in this way is added to 100 grams of spherules of macroporous α-alumina having the characteristics already described in this specification, with a diameter of 8 mm, and heated to 80°C.

While the spherules are kept in rotation, air is passed through at 50 liters/hour and the temperature rises to 120°C in 7 hours.

Carbon dioxide is passed through the spherules at a rate of 30 Nliters/hour and at a pressure of 2.5 atm, the temperature rises to 300°C, and oxygen is then added until the oxygen content in the gas is 20% by volume.

During the addition of oxygen, the temperature is controlled in such a way that it never exceeds 310°C.

The treatment is continued until the carbon dioxide has disappeared from the gas stream after contact with the catalyst.

The total treatment time is about 8 hours.

The catalyst is finally cooled and recovered.

EXAMPLE 2

36 grams of the catalyst spherules prepared as described in Example 1 are loaded into an AISI 316 steel reactor having an internal diameter of 9 mm.

With a temperature of 274°C, a pressure of 11 kg/cm$^2$, a contact time of 1.81 seconds, and a linear velocity of 34 cm/second (measured under the reaction conditions), a gas mixture comprising
ethylene : 9.26% by volume
oxygen: 6.00% by volume
ethane: 0.12% by volume
is passed through the catalyst.

The mixture also contains 10 ppm of acetylene and 0.8 ppm of dichloroethane, the remainder consisting of nitrogen.

By operation under these conditions, one obtains a reaction gas having an ethylene oxide content of 1.2% by volume.

The selectivity of the reaction is 72.1 percent, with an ethylene oxide output of 302 grams per hour per liter of catalyst.

EXAMPLE 3

The catalyst is prepared by the procedure of Example 1 except that the gases, instead of being bled off, are recycled through the spheres of the catalyst being formed at a rate of 5600 Nliters/hour.

EXAMPLE 4

36 grams of the spherules of the catalyst prepared as described in Example 3 are loaded into an AISI 316 steel reactor having an internal diameter of 9 mm.

With a temperature ob 272°C, a pressure of 11 kg/cm$^2$, a contact time of 1.81 seconds, and a space velocity of 12,800 Nliters per liter of catalyst per hour, a gaseous mixture comprising
ethylene: 9.3% by volume
oxygen: 6.1% by volume
ethane: 0.1% by volume
is passed through the catalyst.

The mixture also contains 7 ppm of acetylene and 1.2 ppm of dichloroethane, the remainder consisting of nitrogen.

On operation under these conditions, the conversion of ethylene is 20 percent with a selectivity for ethylene oxide of 73 percent with respect to the reacted ethylene.

The output of ethylene oxide is 340 grams per hour per liter of catalyst.

EXAMPLE 5

2.07 grams of platinum/carbon containing 5% by weight of platinum are added to the solution of silver lactate in lactic acid described in Example 1.

The suspension obtained in this way is added to 207 grams of spherules of macroporous α-alumina having the characteristics already described in this specification, heated to 80°C.

While the spherules are kept in rotation air is passed through at a rate of 50 Nliter/hour and the temperature gradually rises to 160°C in 4 hours.

Nitrogen is passed through the spherules at a rate of 5600 Nliters/hour and at 2.5 atm, and the temperature rises to 300° C.

The introduction of oxygen is then started until the oxygen content in the gas is 20% by volume.

During the addition of oxygen, the temperature is controlled so that it never exceeds 310°C.

The treatment is continued for a total time of about 8 hours, until the carbon dioxide has disappeared from the gases after contact with the catalyst.

EXAMPLE 6

36 grams of spherules of the catalyst prepared in accordance with Example 5 are loaded into an AISI 316 steel reactor having an internal diameter of 9 mm.

With a temperature of 275°C, a pressure of 11 kg/cm$^2$, a contact time of 2.7 seconds, and a space velocity of 8540 Nliters per liter of catalyst per hour, a gaseous mixture comprising
ethylene: 9.25% by volume
oxygen: 6.0% by volume
ethane: 0.12% by volume
passed through the catalyst.

The mixture also contains 7 ppm of acetylene and 1.5 ppm of dichloroethane, the remainder consisting of nitrogen.

On operation under these conditions, a conversion of ethylene of 17 percent, with a selectivity of 71.2 percent with respect to the converted ethylene, is obtained.

The output of ethylene oxide is 188 grams per hour per liter of catalyst.

EXAMPLE 7

A catalyst is prepared by the procedure of Example 1. 36 grams of this catalyst are introduced into the reactor described in Example 2, and ethylene oxide is prepared by introduction of a gaseous stream consisting of:
ethylene: 9.28% by volume
nitrogen: 84.60% by volume
oxygen: 6.00% by volume
ethane: 0.12% by volume The operation is carried out at a pressure of 11 kg/cm$^2$, at a temperature of 265°–267°C, with a linear velocity of the gases of 33.9 cm/second, and with a contact time of 1.81 seconds.

In the drawing curve A shows the variation of the conversion of ethylene (abscissa) as a function of the selectivity of the converted ethylene (ordinate) as found in a series of experiments in which the quantity of dichloroethane was varied from 0.6 ppm (lowermost measuring point) to 1.2 ppm (uppermost measuring point).

EXAMPLE 8

The procedure of Example 1 is followed except that the impregnated particles are heat-treated in air.

36 grams of the catalyst prepared in this way are introduced into the reactor described in Example 2, and ethylene oxide is prepared by introduction of a gaseous stream consisting of:
ethylene: 9.28% by volume
nitrogen: 84.60% by volume
oxygen: 6.00% by volume
ethane: 0.12% by volume The operation is carried out at a temperature of 275°C, at a pressure of 11 kg/cm$^2$, with a linear velocity of the gases of 22.7 cm/second, and with a contact time of 2.71 seconds.

In the drawing curve B shows the variation of the conversion of ethylene (abscissa) as a function of the selectivity with respect to the converted ethylene (ordinate) as found in a series of experiments in which the quantity of dichloroethane was varied from 0.5 ppm (lowermost measuring point) to 1 ppm (uupermost measuring point).

What we claim is:

1. A process for the preparation of silver-based catalysts suitable for the production of ethylene oxide, which comprises impregnating a granular support with a decomposable silver salt selected from the group consisting of the salts of lactic, citric, malic and isomalic acids, drying the impregnated products, and finally heat-treating the dried product at a high temperature, in a gaseous atmosphere containing at least 1% by volume of carbon dioxide.

2. A process in accordance with claim 1, wherein the heat treatment is carried out in a gaseous atmosphere containing at least 50% by volume of carbon dioxide.

3. A process in accordance with claim 1, wherein the heat treatment is carried out at a temperature of from about 270° to 350°C.

4. A process in accordance with claim 1, wherein the heat treatment is carried out at a temperature of from about 290° to 310°C in a gaseous atmosphere containing more than 70% by volume of carbon dioxide.

5. A process in accordance with claim 1, wherein the heat treatment is carried out in the presence of a gaseous atmosphere containing at least 0.01% by volume of oxygen.

6. A process in accordance with claim 1, wherein the heat treatment is carried out in a gaseous atmosphere containing about 1 to 20% by volume of oxygen.

7. A process in accordance with claim 1, wherein during the heat treatment the gaseous atmosphere is recycled through the particles of the catalyst being formed at a rate of from about 10 to 10,000 liters per hour per kg of catalyst.

8. A process in accordance with claim 1, wherein the treatment is carried out for times from between about 5 to about 10 hours.

9. A process in accordance with claim 1 wherein during the heat treatment the gaseous atmosphere is maintained at a pressure of from about 1 to 20 kg/cm$^2$.

10. A process in accordance with claim 1, wherein the support materials consist of alumina, silicon carbide, and magnesium oxide.

11. A process in accordance with claim 1, wherein the support consists of $\alpha$-alumina having a surface area of from about 0.01 to 1.0 m$^2$/gram, a porosity of about 10 to 50 percent, and an average pore diameter of from about 20 to 180 microns.

12. A process in accordance with claim 1, wherein the support is in the form of spherules having a diameter of from about 4 to 9 mm.

13. A process in accordance with claim 1, wherein the support is impregnated with the decomposable silver salt with operation at a temperature of from about 60° to 115°C with a quantity of salt such as to ensure a quantity of silver of from about 7 to 30% by weight with respect to the support.

14. A process in accordance with claim 1, wherein in the impregnation phase, promoters selected from the group consisting of gold, palladium, and platinum are added in quantities of from about 0.01 to 1.0% by weight with respect to the metallic silver.

15. A process in accordance with claim 1, wherein in the impregnation phase, promoters such as barium and calcium, in the form of salts of lactic acid, are added in quantities of from about 0.1 to 5 moles per 100 gram atoms of silver.

16. A process in accordance with claim 1, wherein the drying is carried out at temperatures rising to a maximum of about 160°C and for times of from about 1 to 10 hours.

17. A process in accordance with claim 1, wherein oxygen is added to said gaseous atmosphere in steadily increasing quantities up to an oxygen content of not less than about 0.01% by volume.

18. A process in accordance with claim 17, wherein the oxygen is added in steadily increasing quantities up to an oxygen content between 1 and 20% by volume over 5–10 hours.

19. A process in accordance with claim 1, wherein in the impregnation phase promoters selected from the group consisting of palladium on carbon, platinum on carbon and carbon impregnated with colloidal platinum are added.

* * * * *